(12) United States Patent
Dultz (10) Patent No.: US 7,981,664 B1
(45) Date of Patent: Jul. 19, 2011

(54) APPARATUS AND METHOD FOR PERFORMING LIGAND BINDING ASSAYS ON MICROARRAYS IN MULTIWELL PLATES

(75) Inventor: Shane C Dultz, Westlake Village, CA (US)

(73) Assignee: Maven Technologies, LLC, Los Angeles, CA (US)

( * ) Notice: Subject to any disclaimer, the term of this patent is extended or adjusted under 35 U.S.C. 154(b) by 500 days.

(21) Appl. No.: 12/125,685

(22) Filed: May 22, 2008

(51) Int. Cl.
*C12M 3/00* (2006.01)

(52) U.S. Cl. .................. 435/287.2; 422/407; 422/82.11; 435/288.4; 436/518; 436/524; 436/531; 436/164; 436/805; 436/809

(58) Field of Classification Search .................. None
See application file for complete search history.

(56) References Cited

U.S. PATENT DOCUMENTS

| | | | |
|---|---|---|---|
| 1,637,141 A | 7/1927 | Cooper | |
| 3,858,616 A | 1/1975 | Thiery et al. | |
| 4,146,364 A | 3/1979 | McCormick | |
| 4,238,565 A | 12/1980 | Hornby et al. | |
| 4,256,834 A | 3/1981 | Zuk et al. | |
| 4,508,832 A | 4/1985 | Carter et al. | |
| 5,164,589 A | 11/1992 | Sjoedin | |
| 5,225,164 A | 7/1993 | Astle | |
| 5,229,833 A | 7/1993 | Stewart | |
| 5,234,769 A | 8/1993 | Shevlin | |
| 5,255,075 A | 10/1993 | Cush | |
| 5,313,264 A | 5/1994 | Ivarsson et al. | |
| 5,341,215 A | 8/1994 | Seher | |
| 5,437,840 A | 8/1995 | King et al. | |
| 5,446,534 A | 8/1995 | Goldman | |
| 5,483,346 A | 1/1996 | Butzer | |
| 5,485,277 A | 1/1996 | Foster | |
| 5,491,097 A | 2/1996 | Ribi et al. | |
| 5,491,556 A | 2/1996 | Stewart et al. | |
| 5,573,956 A | 11/1996 | Hanning | |
| 5,593,130 A | 1/1997 | Hansson et al. | |
| 5,633,724 A | 5/1997 | King et al. | |
| 5,641,640 A | 6/1997 | Hanning | |
| RE35,716 E | 1/1998 | Stapleton et al. | |
| 5,738,825 A | 4/1998 | Rudigier et al. | |
| 5,753,518 A | 5/1998 | Karlsson | |

(Continued)

FOREIGN PATENT DOCUMENTS

AU 742417 2/2000

(Continued)

OTHER PUBLICATIONS

Tadashi Saitoh, et al."Optical Characterization of Very Thin Hydrogenated Amorphous Silicon Films Using Spectroscopic Ellipsometry"; Japanese Journal of Applied Physics; vol. 30, No. 11B, Nov. 1991. pp. L1914-L1916.

(Continued)

*Primary Examiner* — Chris L Chin
(74) *Attorney, Agent, or Firm* — Haynes and Boone, LLP (57) ABSTRACT

Each well of a multiwell plate adapted to accept a plurality of biological samples for testing for the presence of analytes in the sample is further adapted herein for immobilizing on the side walls of a well a 3D arrangement of ligand arrays. A well is formed with planar side walls and a stack of sample separators is placed within a well in positions so as to not come in contact with ligand spots in the array(s). The spacing between each pair of adjacent separators in a stack forms a sample chamber in a position corresponding to an array of the 3D arrangement of ligand arrays.

20 Claims, 8 Drawing Sheets

U.S. PATENT DOCUMENTS

| | | | |
|---|---|---|---|
| 5,796,858 | A | 8/1998 | Zhou et al. |
| 5,813,439 | A | 9/1998 | Herrero et al. |
| 5,856,873 | A | 1/1999 | Naya et al. |
| 5,922,594 | A | 7/1999 | Loefas |
| 5,922,604 | A | 7/1999 | Stapleton et al. |
| 5,955,729 | A | 9/1999 | Nelson et al. |
| 5,965,456 | A | 10/1999 | Malmqvist et al. |
| 5,972,612 | A | 10/1999 | Malmqvist et al. |
| 6,008,010 | A | 12/1999 | Greenberger et al. |
| 6,008,893 | A | 12/1999 | Roos et al. |
| 6,026,053 | A | 2/2000 | Satorius |
| 6,045,996 | A | 4/2000 | Cronin et al. |
| 6,065,501 | A | 5/2000 | Feret et al. |
| 6,127,183 | A | 10/2000 | Ivarsson et al. |
| 6,140,044 | A | 10/2000 | Besemer et al. |
| 6,143,513 | A | 11/2000 | Loefas |
| 6,143,574 | A | 11/2000 | Karlsson et al. |
| 6,197,595 | B1 | 3/2001 | Anderson et al. |
| 6,200,814 | B1 | 3/2001 | Malmqvist et al. |
| 6,207,381 | B1 | 3/2001 | Larsson et al. |
| 6,253,793 | B1 | 7/2001 | Dupoiron et al. |
| 6,277,330 | B1 | 8/2001 | Liu et al. |
| 6,289,286 | B1 | 9/2001 | Andersson et al. |
| 6,354,333 | B1 | 3/2002 | Dupoiron et al. |
| 6,355,429 | B1 | 3/2002 | Nygren et al. |
| 6,415,825 | B1 | 7/2002 | Dupoiron et al. |
| 6,475,809 | B1 | 11/2002 | Wagner et al. |
| 6,493,097 | B1 | 12/2002 | Ivarsson |
| 6,503,760 | B2 | 1/2003 | Malmqvist et al. |
| D472,644 | S | 4/2003 | Dawson et al. |
| 6,549,011 | B2 | 4/2003 | Flatt |
| 6,589,798 | B1 | 7/2003 | Loefas |
| 6,594,011 | B1 | 7/2003 | Kempen |
| D480,149 | S | 9/2003 | Dawson et al. |
| 6,698,454 | B2 | 3/2004 | Sjoelander et al. |
| 6,710,870 | B1 | 3/2004 | Marowsky et al. |
| 6,714,303 | B2 | 3/2004 | Ivarsson |
| 6,806,051 | B2 | 10/2004 | Ellson |
| 6,833,920 | B2 | 12/2004 | Rassman et al. |
| 6,840,286 | B2 | 1/2005 | Espinasse et al. |
| 6,859,280 | B2 | 2/2005 | Kempen |
| 6,882,420 | B2 | 4/2005 | Rassman et al. |
| 6,981,526 | B2 | 1/2006 | Glejbol et al. |
| 7,045,287 | B2 | 5/2006 | Smith et al. |
| 7,193,711 | B2 | 3/2007 | Rassman et al. |
| 7,195,872 | B2 | 3/2007 | Agrawal et al. |
| 2002/0019019 | A1 | 2/2002 | Hamalainen et al. |
| 2002/0154311 | A1 | 10/2002 | Ivarsson |
| 2002/0182717 | A1 | 12/2002 | Karlsson |
| 2003/0022388 | A1 | 1/2003 | Roos et al. |
| 2003/0067612 | A1 | 4/2003 | Ivarsson |
| 2003/0112432 | A1 | 6/2003 | Yguerabide et al. |
| 2003/0148401 | A1 | 8/2003 | Agrawal et al. |
| 2003/0205681 | A1 | 11/2003 | Modlin |
| 2003/0232384 | A1 | 12/2003 | Kocher et al. |
| 2004/0002167 | A1 | 1/2004 | Andersson et al. |
| 2004/0012676 | A1 | 1/2004 | Weiner et al. |
| 2004/0023247 | A1 | 2/2004 | Xu et al. |
| 2004/0030504 | A1 | 2/2004 | Helt et al. |
| 2004/0038268 | A1 | 2/2004 | Pirrung et al. |
| 2005/0148063 | A1 | 7/2005 | Cracauer et al. |

FOREIGN PATENT DOCUMENTS

| | | |
|---|---|---|
| WO | WO 8911057 | 11/1989 |
| WO | WO 9100467 | 1/1991 |
| WO | WO 96/08720 | 3/1996 |
| WO | WO 96/38729 | 12/1996 |
| WO | WO 97/19375 | 5/1997 |
| WO | WO 98/32002 | 7/1998 |
| WO | WO 03/056337 A1 | 7/2003 |
| WO | WO 03/102580 A1 | 12/2003 |

OTHER PUBLICATIONS

"Handbook of Optics", Michael Bass Editor in Chief, by the Optical Society of America; vol. 1; pp. 4.23, 4.24; 1995 McGraw-Hill, Inc.

Bass, et al. "Handbook of Optics", by The Optical Society of America; vol. 1; Section 41.10; 1995 McGraw-Hill, Inc.

Gang Jin et al. "Imaging Ellipsometry Revisited: Developments for Visualization of Thin Transparent Layers on Silicon Substrates", American Institute of Physics, Rev. Sci. Instrum., pp. 2930-2936, Aug. 1996.

Max Born et al. "Principles of Optics—Electromagnetic Theory of Propagation, Interference and Diffraction of Light", Sixth Edition, pp. 47-51 Pergamon Press, 1980.

Eggins, "Biosensors: An Introduction", pp. 112-113, 1987 John Wiley & Sons.

Danny Van Noort et al. "Monitoring Specific Interaction of Low Molecular Weight Biomolecules on Oxidized Porous Silicon Using Ellipsometry", Biosensors & Bioelectronics vol. 13, No. 3-4 pp. 439-449, 1998 Elsevier Science, S.A. Great Britain.

Gang Jin et al. "Imaging Ellipsometry for Biosensor Applications" Transducers '95. Eurosensors IX, Digest of Technical Papers vol. 2, Sessions A7-D13, Papers No. 232-496 pp. 509-512, Stockholm, Sweden, Jun. 1995.

Jinyu Wang "Waveguide Ellipsometry Biosensors: Concept and Preliminary Analysis", SPIE vol. 1648, Fiber Optical Medical and Fluorescent Sensors and Applications pp. 44-50, 1992.

Ulf Jonsson et al. "Flow-Injection Ellipsometry—An in Situ Method for the Study of Biomolecular Adsorption and Interaction at Solid Surfaces," Colloids and Surfaces, 13 (1985) pp. 333-339, 1985 Elsevier Science Publishers BV, Amsterdam, The Netherlands.

Jonsson, Ulf et al. "Biosensors Based on Surface Concentration Measuring Devices-The Concept of Surface Concentration" Progress in Colloid and Polymer Sci. vol. 70, pp. 96-100, 1985.

Schena, Mark "DNA Microarrays: A Practical Approach" Edited by Mark Schena, Department of Biochemistry, Beckman Center, Stanford University Medical Center, Stanford, USA, Oxford University Press, 1999.

Schema, PhD. Mark, "Microarray Biochip Technology" TeleChem International, Inc., Sunnyvale, California, USA, A BioTechniques Books Publication, Eaton Publishing, pp. 10-11, 2000.

Harland G. Tompkins, et al. "Spectroscopic Ellipsometry and Reflectometry a User's Guide" A Wiley-Interscience Publication, John Wiley & Sons, Inc., 1999.

Ulf Jonsson et al. "Surface Immobilization Techniques in Combination with Ellipsometry" Methods in Enzymology vol. 137, Immobilized Enzymes and Cells Part D pp. 381-1351, 1988 Academic Press, Inc. Harcourt Brace Jovanovich, Publishers.

Ch Striebel et al. "Characterization of Biomembranes by Spectral Ellipsometry, Surface Plasmon Resonance and Interferometry with Regard to Biosensor Application", Biosensors & Bioelectronics 9, pp. 139-146, 1994 Elsevier Science Publishers Ltd.

T.A. Ruzgas et al. "Ellipsometric Immunosensors for the Determination of γ-Interferon and Human Serum Albumin", Biosensors & Bioelectronics 7, pp. 305-308, 1992 Elsevier Science Publishers Ltd.

Haken Nygren et al. "Determination by Ellipsometry of the Affinity of Monoclonal Antibodies", Journal of Immunological Methods, 92, pp. 219-225, 1986 Elsevier Science Publishers Ltd.

John F. Place et al. "Opto-electronic Immunosensors: A Review of Optical Immunoassay at Continuous Surfaces", Biosensors 1, pp. 321-353, 1985 Elsevier Applied Science Publishers Ltd., England.

A. Brecht et al. "Biosensors: Fundamentals, Technologies and Applications" GBF Monographs, vol. 17, pp. 174-178, 1991 Germany.

Hakan Nygren et al. "Kinetics of Antibody-Binding to Surface-Immobilized Antigen: Influence of Mass Transport on the Enzyme-Linked Immunosorbent Assay (ELISA)", Journal of Colloid and Interface Science, vol. 107, No. 2 pp. 560-566, Oct. 1985 Academic Press, Inc.

Martin Malmsten et al. "Effects of Hydrophilization and Immobilization on the Interfacial Behavior of Immunoglobulins", Journal of Colloid and Interface Sicence 177, pp. 70-78, 1996 Academic Press, Inc.

Pentti Tengvall et al. "Temporal Studies on the Deposition of Complement on Human Colostrum IgA and Serum Immobilized on Methylated Silicon", Journal of Biomedical Materials Research, vol. 35, pp. 81-91, 1997 John Wiley & Sons, Inc.

Huaiyou Wang et al. "Assembly of Antibodies in Lipid Membranes for Biosensor Development", Applied Biochemistry and Biotechnology, vol. 53 pp. 163-181, 1995 Humana Press Inc.

G. Elender et al. "Wetting and Dewetting of Si/SiO2-Wafers by Free and Lipid-Monolayer Covered Aqueous Solutions Under Controlled Humidity", Journal de Physique, II France 4 pp. 455-479, Mar. 1994.

C.F. Mandenius et al. "Coupling of Biomolecules to Silicon Surfaces for use in ellipsometry and other related techniques", Methods in Enzymology, vol. 137, pp. 389-394, 1988 Academic Press, Inc.

A.W. Flounders et al. "Patterning of immobilized antibody layers via photolithography and oxygen plasma exposure", Biosensors and Bioelectronics, vol. 12, No. 6 pp. 447-456, 1997 Elsevier Science Ltd., Great Britain.

A. Ahluwalia et al. "A comparative study of protein immobilization techniques for optical immunosensors", Biosensors and Bioelectronics 7, (1991) pp. 207-214, 1992 Elsevier Science Publishers Ltd.

Dr. Rudolf Oldenbourg "Metamorph Imaging System", http://www.image1.com/products/metapolscope/ Universal Imaging Corporation Last Updated Jun. 10, 1999 pp. 1-2.

Dr. Rudolf Oldenbourg "A new view on polarization microscopy", Nature, vol. 381, pp. 811-812, Jun. 27, 1996.

Clifford C. Hoyt et al. "Structural analysis with quantitative birefringence imaging", American Laboratory, pp. 34-42, Jul. 1999.

Dirk Honig et al. "Direct visualization of monolayers at the air-water interface by Brewster angle microscopy", J. Phys. Chem., pp. 4590 & 4592, 1991 American Chemical Society.

S. Henon et al. "Microscope at the Brewster angle: direct observation of first-order phase transitions in monolayers", Rev. Sci. Instrum. 62, (4) pp. 936-939, Apr. 1991 American Institute of Physics.

Gang Jin et al. "A biosensor concept based on imaging ellipsometry for visualization of biomolecular interactions", Analytical Biochemistry 232, pp. 69-72, 1995.

Pentti Tengvall et al. "Complement activation by 3-mercapto-1,2-propanediol immobilized on gold surfaces", Biomaterials vol. 17, No. 10 pp. 1001-1007, 1995 Elsevier Science Ltd., Great Britain.

H. Arwin "Spectroscopic ellipsometry and biology: recent developments and challenges", Thin Solid Films 313-314, pp. 7640774, 1998 Elsevier Science S.A.

Christopher Palmer "Diffraction Grating Handbook", pp. 35-44, 2000 Richardson Grating Laboratory, Rochester, New York.

Erwin G. Loewen "Diffraction Gratings, Ruled and Holographic", Applied Optics and Optical Engineering, vol. IX, pp. 33-71, Bausch and Lomb, Inc., Rochester, New York 1983 Academic Press, Inc.

Willems, Goerge M., et al., Adsorption and Conversion of Prothrombin on a Rotating Disc, Blood, Jul. 15 1993, vol. 82, No. 2, pp. 497-504.

U.S. Appl. No. 11/677,674, Dultz et al.
U.S. Appl. No. 11/748,023, Dultz et al.
U.S. Appl. No. 11/696,369, Dultz.
U.S. Appl. No. 11/752,056, Dultz.
U.S. Appl. No. 12/125,735, Dultz et al.
U.S. Appl. No. 12/650,327, Dultz et al.

FIG. 6C

APPARATUS AND METHOD FOR PERFORMING LIGAND BINDING ASSAYS ON MICROARRAYS IN MULTIWELL PLATES

CROSS-REFERENCE TO RELATED APPLICATIONS

This application is related to pending U.S. application Ser. No. 11/677,674, filed Feb. 22, 2007, pending U.S. application Ser. No. 11/748,023, filed May 14, 2007, pending U.S. application Ser. No. 11/696,369, filed Apr. 4, 2007, and pending U.S. application Ser. No. 11/752,056, filed May 22, 2007, the contents of which are incorporated by reference herein for all purposes.

FIELD OF THE INVENTION

This invention relates to an apparatus for characterizing molecular binding events for performing binding protein assays and more particularly to such systems employing microarrays.

BACKGROUND

U.S. Pat. No. 6,594,011 issued Jul. 15, 2003, the entirety of which is incorporated by reference herein for all purposes, discloses an imaging apparatus and method for real time imaging ellipsometry for high throughput sensing of binding events useful in molecular interaction analysis including biotech applications. The apparatus and method disclosed employ the immobilization of an array of binding or capture molecules ("ligands") on a planar surface of a transparent substrate and the use of a beam of polarized light directed at the underside of the surface in a manner to achieve total internal reflection (TIR) and generate an evanescent field in the plane of the ligands. The ligands are exposed to a biological sample and analytes in the biological sample bind to different patterns of the immobilized ligands in a manner to change the polarization at locations in the array at which binding occurs. An image of the array is compared with a stored image of the initial light polarization shifts to determine the location and magnitude of binding events within the array, thus identifying and quantitating the analytes present in the biological sample.

The apparatus for implementing the foregoing technique typically employs a prism or gratings to achieve the requisite TIR generated evanescent field, the prism being the more practical implementation.

TIR imaging ellipsometry works well for fields of view up to 1-2 cm$^2$, which permits real time imaging of tens of thousands of binding events simultaneously. However, there is a need to be able to image or scan areas which are much larger, such as 128 mm×86 mm (e.g., the area of a 384 well or a 96 multiwell plate) to permit lower costs per test and for multiple tests per patient for large numbers of patients simultaneously which is increasingly a requirement for more clinical diagnostics and personalized medicine. Obviating the need for a single large prism simplifies both the instrument and disposable multiwell plate.

Co-pending U.S. application Ser. No. 11/696,369, filed Apr. 4, 2007, the entirety of which is incorporated by reference herein for all purposes, discloses a multiwell plate in which arrays of ligands are printed on planar side walls of the liquid reservoirs, or wells. The plate is fabricated with transparent material, such as glass or plastic, and a beam of light is directed upwards from the bottom of the plate into the separation between adjacent wells. The direction of the beam is chosen to achieve total internal reflection (TIR) at a well side wall in a manner to generate an evanescent field in the plane of an array of ligands on the interior face of that well. The reflected light from the side wall carries binding information between analytes in a biological sample in the selected well and different patterns of capture molecules in the array immobilized on the addressed side wall.

SUMMARY

In accordance with the principles of this invention, a plurality of independent array patterns is immobilized in a stacked format on a single planar wall of a well to correspond to multiple sample chambers stacked along the vertical axis of a well. A corresponding number of separators are formed in the well resulting in a stack of "sample chambers", with each chamber capable of containing a biological sample, and each sample chamber positioned with respect to a different one of the "vertical" stack of immobilized arrays.

A sample including analytes is introduced to each chamber with (for example) a hypodermic needle which is advanced through the separators in the stack to introduce a sample to a selected chamber. Any opening for the needle in any separator between a selected chamber and the top of a well is small and is the site of an air bubble which permits adjacent chambers in a stack to provide space for a sample without mixing samples.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

Embodiments of the present invention and their advantages are best understood by referring to the detailed description that follows. It should be appreciated that like reference numerals are used to identify like elements illustrated in one or more of the figures. It should also be appreciated that the figures may not be necessarily drawn to scale.

DETAILED DESCRIPTION

The present invention provides an advantageous apparatus and method for performing ligand binding assays using microarrays in a multiwell plate format. Prior to describing embodiments of the present invention in detail, the following definitions are provided for use throughout the present document.

DEFINITIONS

Microwell Plate: A flat plate with multiple "wells" used like small test tubes. The microwell plate has become a standard tool in analytical research and clinical diagnostic testing laboratories with 6, 24, 96, 384 or even 1536 sample wells arranged in a 2:3 rectangular matrix in one example.

Ligand: Any molecule that binds to another, in normal usage a soluble molecule such as a hormone or biological molecule that binds to a binding partner or capture molecule. The decision as to which is the ligand and which is the capture molecule is often arbitrary. In the sense of this invention, the ligand refers to that binding element attached to a planar surface and which binds to an analyte molecule in a biological sample.

Total Internal Reflection (TIR): An optical phenomenon that occurs when light strikes a medium boundary at a steep angle. If the refractive index is lower on the other side of the boundary (i.e., the side that does not directly receive the light), no light can pass through and effectively all of the light is reflected. The critical angle is the angle of incidence where total internal reflection begins and continues up to angles of incidence of 90 degrees.

Ellipsometry: A very sensitive optical measurement technique providing capabilities for thin film analysis utilizing the change of polarization of light which is reflected off a sample or transmitted through a sample.

Surface Plasmon Resonance (SPR): The excitation of surface plasmons by light is denoted as a surface plasmon resonance for planar surfaces. Plasmons are collective oscillations of large numbers of electrons in matter, mostly in metals.

Arrays: Ligands affixed to a surface at separate localized regions called spots in an ordered manner thus forming a microscopic pattern where ligand identity is determined by the location (or "address") of that particular spot.

Binding Protein (Ligand) Assay: A test that uses the binding of proteins (e.g., antibodies) to other ligands (e.g., antigens) to identify and measure the concentration of certain biological substances in blood, urine or other body components. Ligand assays may be used to diagnose disease, drug or vitamin levels, response to therapy or other information of biological relevance. Also, test results can provide information about a disease that may help in planning treatment (for example, when estrogen receptors are measured in breast cancer).

Introducer: The term "introducer" means any instrumentation to introduce a sample into a well. This may include a hypodermic needle, a cannula, a pipette or capillary which may or may not use a preexisting hole in a succession of sample chambers. This may include a multiple "tine" comb-like structure with different length "tines" each with a central channel and where the lengths correspond to the position in the stack of the sample chambers serviced by the sample introducer tine.

Beam: The illuminating beam may or may not be polarized. If polarized, the pattern of the localized changes in the phase of s- and p-polarized light is measured. The system can also be adapted for surface plasma resonance by employing a thin metallic film beneath the ligands as is well understood in the art for producing a surface plasmon interaction.

Insert: An "insert" is defined as an apparatus which provides one or more sample separators to provide multiple sample chambers in a well to allow for 3D stacking of the samples within a single well. The insert need not be transparent nor have stringent surface roughness requirements necessary for good optical surfaces. The insert is made to be placed into wells of a plate in such a manner that sample liquid does not leak between the insert and side walls of the well.

Liner: The liner is a transparent material on which the ligand spots are deposited. The material is typically glass, plastic, or a combination thereof.

Well: A well is any recess in a base plate which is adapted to receive an insert and accept a sample or a multitude of samples.

Side walls: Side walls are the well walls and are preferably planar in order to properly image binding events with the immobilized array pattern. The description is primarily in terms of a four-sided well configuration, but the well can be rectangular, hexagonal, or a variety of geometries as long as each wall is planar. The preferred orientation of a wall is normal to the plane of the base plate on which the walls are formed in order to simplify the positioning of the illumination system to achieve total internal reflection. The necessity of having a planar wall is for current imaging ellipsometry practice. It is contemplated that practical results may also be obtained by "line" scanning a curved wall.

Between Well Spacing: The "between well spacing" is the separation between adjacent wells and has to meet specific dimensions in order to allow total internal reflection to occur and to produce the necessary evanescent field in the plane of the array of ligands. The spacing may be filled by transparent material integral with the base plate or by a liner which is added to complete the individual well structure.

Sample: A sample is any biological material which may include analytes which may bind to different patterns of ligands.

3D: The term "3D" applies to the formation of a stratum of separate arrays of ligands on a single face in a single well. The individual arrays are conveniently elongated in a direction horizontal to the well axis and are accessed by a set of sample chambers inserted into a well where each chamber aligns with a corresponding array of the strata of arrays vertically positioned on a wall of a well. An array stratum may be immobilized on each wall of a well. For an insert of seven chambers for example, a single square-shaped well provides for twenty-eight individual tests. This number can be extended by including different patterns of ligands in each of the arrays.

Interface: The interface is defined as the plane where two optical components come together in the optical path of the illuminating beam. The interface is formed in the presence of an index matching medium which renders the interface optically transparent when the components have the same index of refraction.

Figure 1:
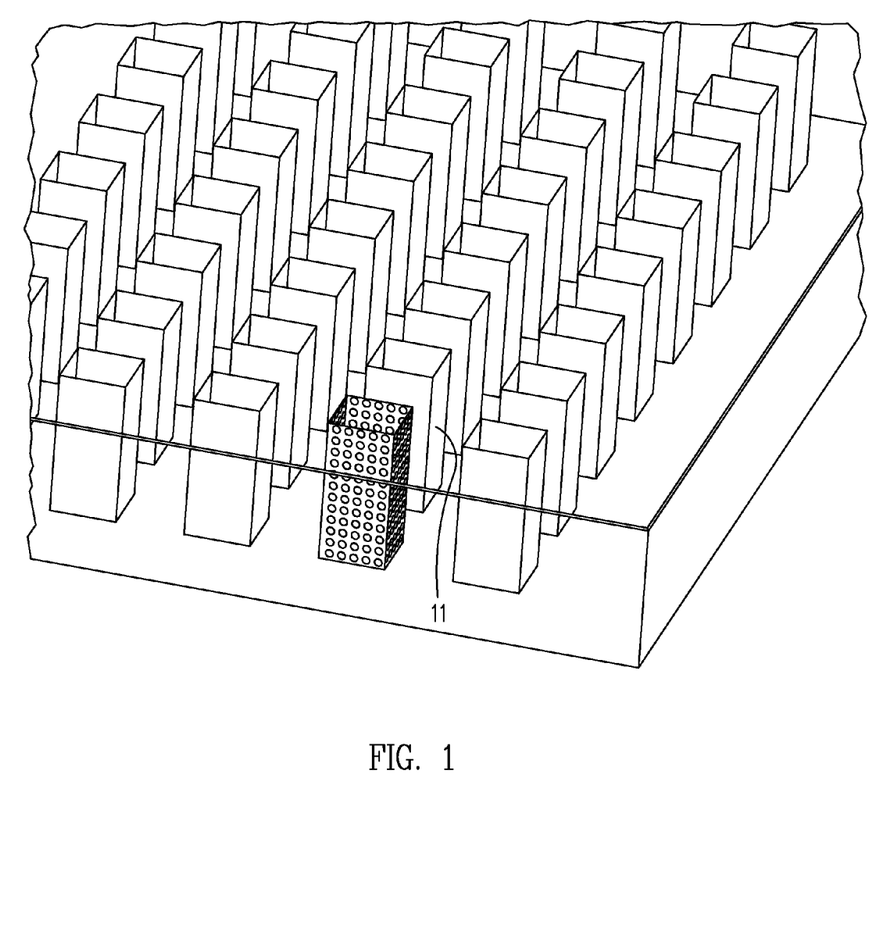
FIG. 1 is a projection view of a portion of a multiwell plate with planar side walls on which array patterns of ligands can be immobilized in accordance with the principles of this invention.

FIG. 1 is a projection view of a portion of an illustrative ninety-six well multiwell plate 11. The plate normally is positioned in a tray (not shown) for movement with respect to an illumination and a measuring and/or sensing subassembly as is discussed hereinafter. Plate 11 is typically organized in rows and columns of eight and twelve wells, respectively.

Figure 2A:
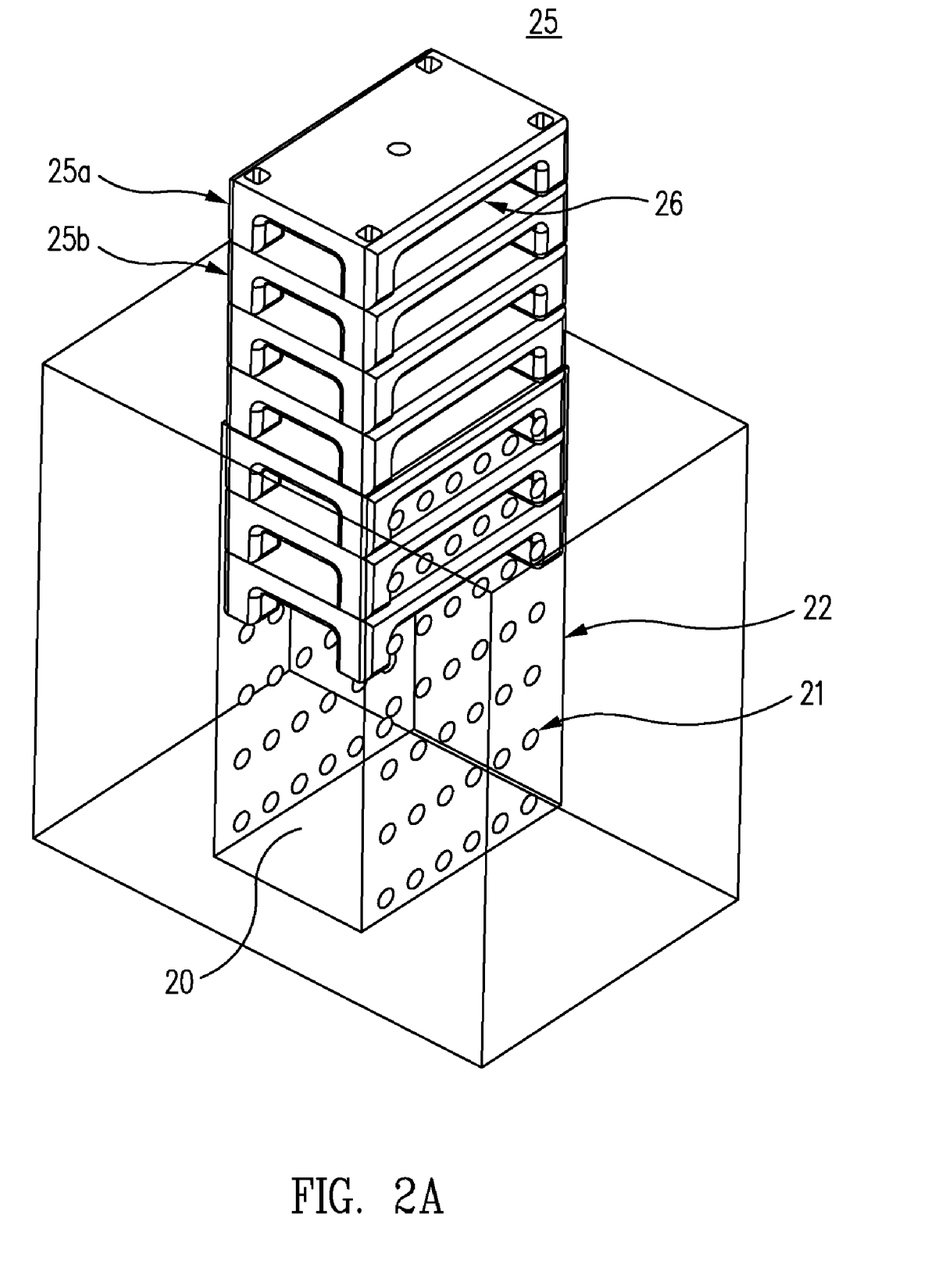
FIG. 2A is a schematic view of a portion of the plate of FIG. 1 showing a stack of immobilized arrays each aligned horizontally with a multilevel sample positioning insert.
Figure 2B:
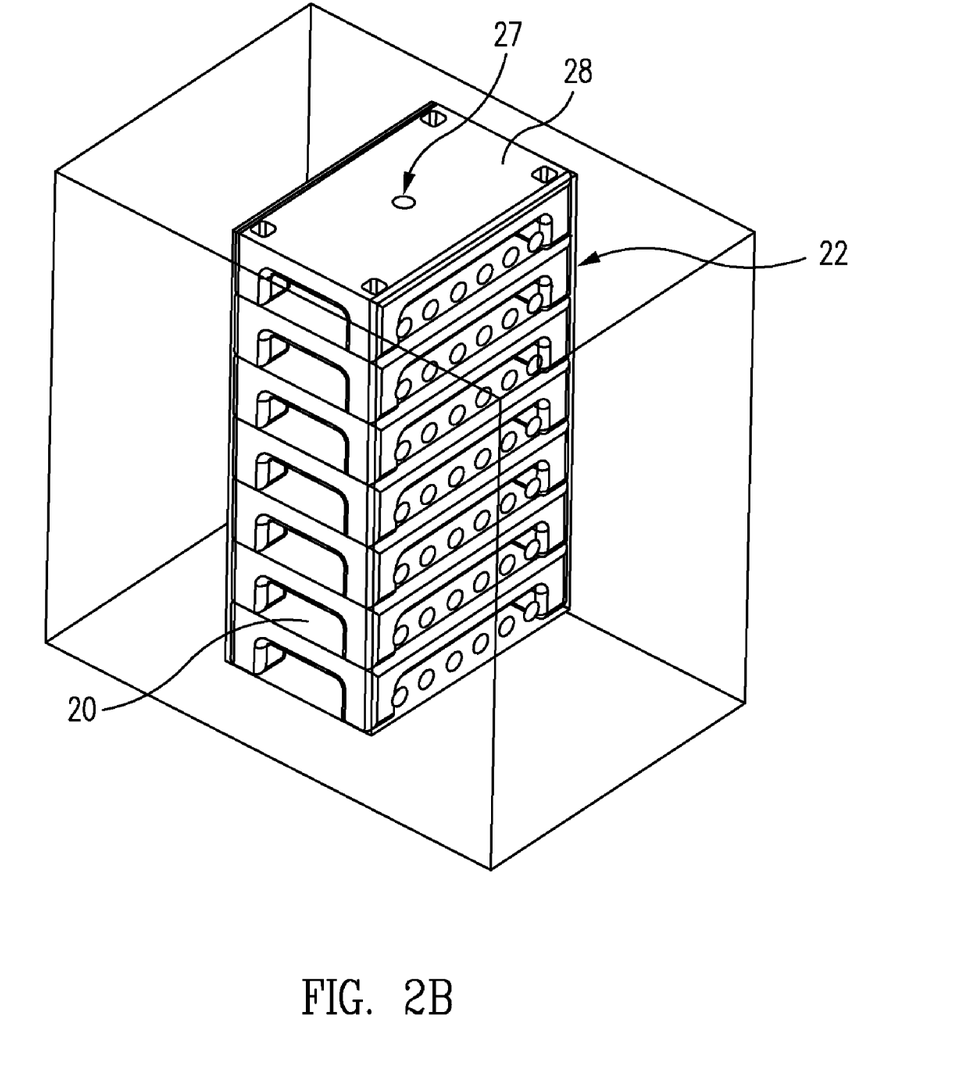
FIG. 2B is a schematic view of the well shown in FIG. 2A showing the final position of the insert.

FIGS. 2A and 2B are schematic representations of a well 20 defined within an encompassing portion of plate 11. The dimensions and specifications for the encompassing portion are important and discussed more fully hereinafter. The well has at least one planar side wall and an array pattern or multiple array patterns are immobilized on that side wall. In FIGS. 2A-2B, well 20 is shown illustratively with four planar walls in a rectangular configuration and seven arrays 21 are shown immobilized on a wall 22 of the well. The arrays are visualized in a stack of horizontal linear patterns spaced apart along the vertical axis of the well but since the entire side wall may be imaged, various patterns are possible for the ligand spots.

An insert 25 is adapted for introduction into well 20. The insert has defined within it a number of sample chambers 25a (seven are illustrated as an example in FIGS. 2A-2B), each of which has, when fully inserted, an open face 26 opposite an array of immobilized ligands. For an array stack immobilized on a single wall of a well, only one face of a chamber need be open.

FIG. 2B shows insert 25 fully seated in well 20. It can be seen from the figure that an open face of a chamber is in position corresponding to an (illustratively horizontal linear) array in the stack of arrays. Thus, each array, which of course need not be linear, is positioned to bind with analytes in a sample introduced to the associated sample chamber of the insert 25.

Figure 3:
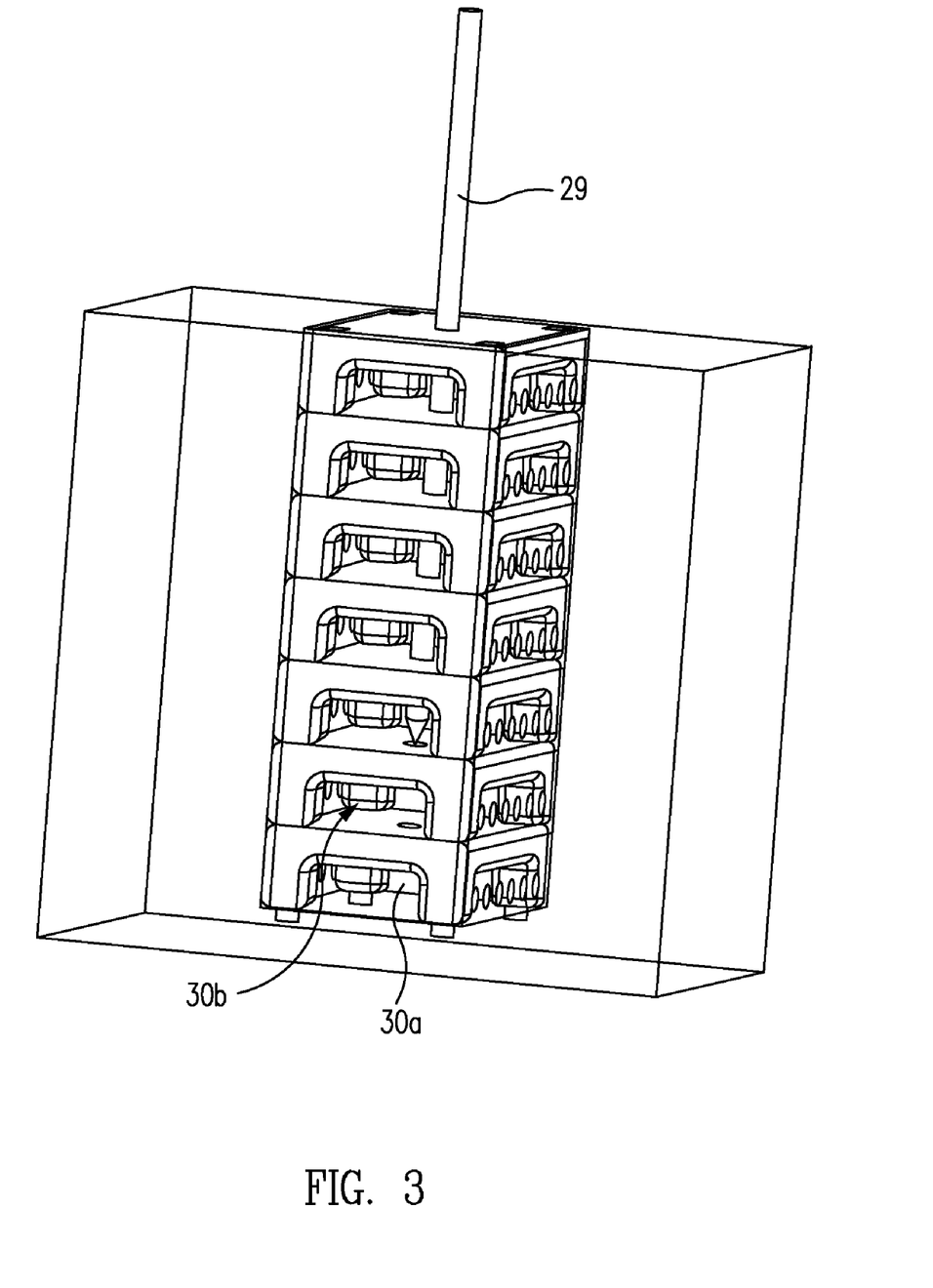
FIG. 3 is a schematic view of the portion of a plate as shown in FIG. 2B also showing a sample introduction implementation (introducer)

Samples are introduced to the sample chambers of the insert through apertures 27 in top surfaces 28 of the sample chambers 30 as shown in FIGS. 2A-2B, 3, and 4. To this end, an introducer such as a tube 29 is inserted into apertures 27 and advanced to a lowest sample chamber 30a as illustrated in FIG. 3. A sample is introduced into chamber 30a and the tube is withdrawn to a position for introducing a (different) sample into a different sample chamber, such as sample chamber 30b. The procedure repeats until all the seven sample chambers are filled with (e.g., different) samples and tube 29 is withdrawn. The samples will not mix because of the small sizes of the holes made by the introduction of tube 29 and by the presence of an air bubble at each hole.

It is to be understood that the immobilization of horizontal patterns of ligands in a stack on a wall of a well provides for a 3D arrangement of independent tests. Thus for a ninety-six well plate, seven arrays on only a single wall of each well permits 672 individual assays to be carried out. For wells with rectangular geometries, four times as many assays (2688) are permitted.

Figure 4:
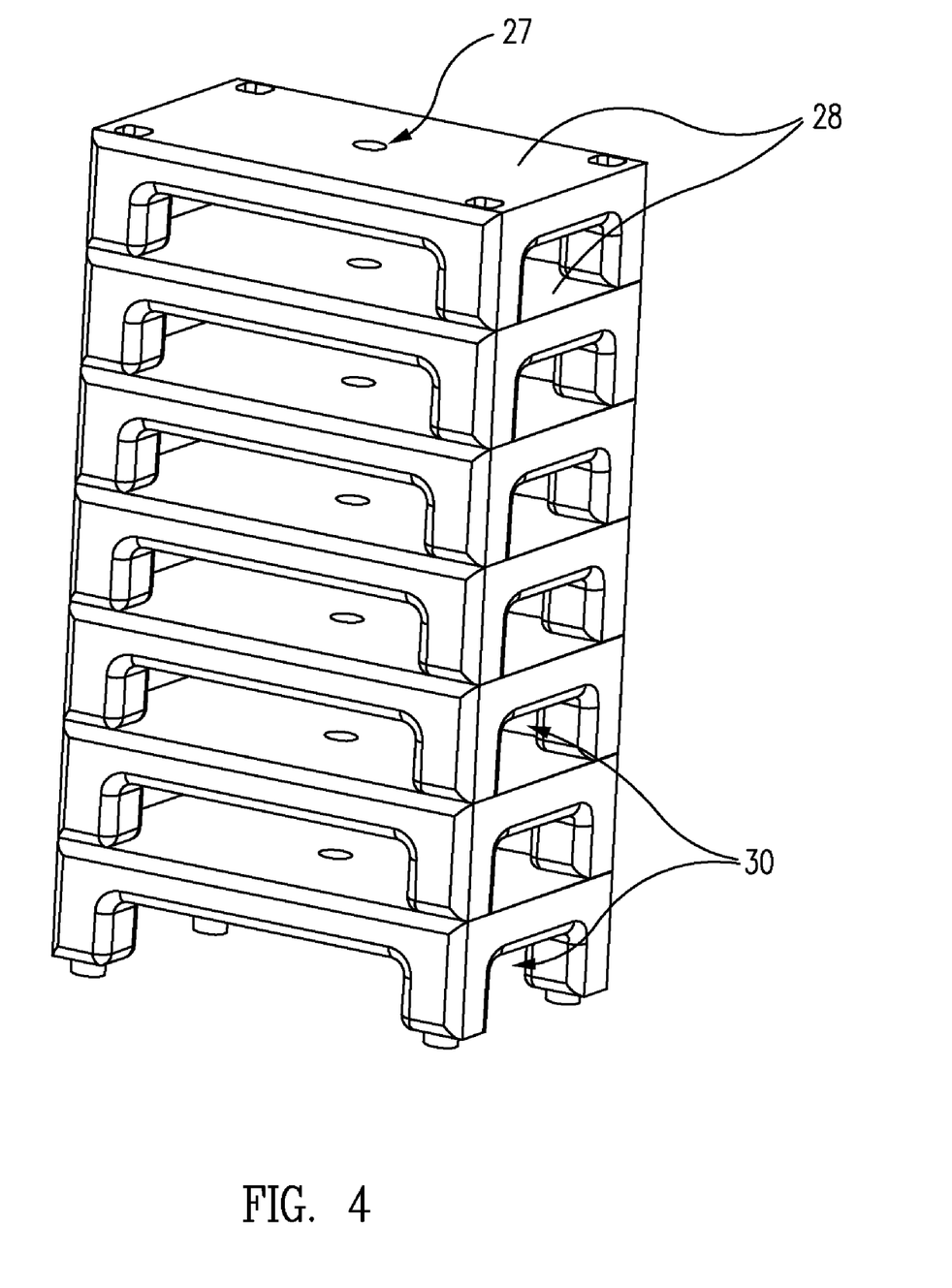
FIG. 4 is a schematic view of the insert in accordance with an embodiment of the present invention.
Figure 5:
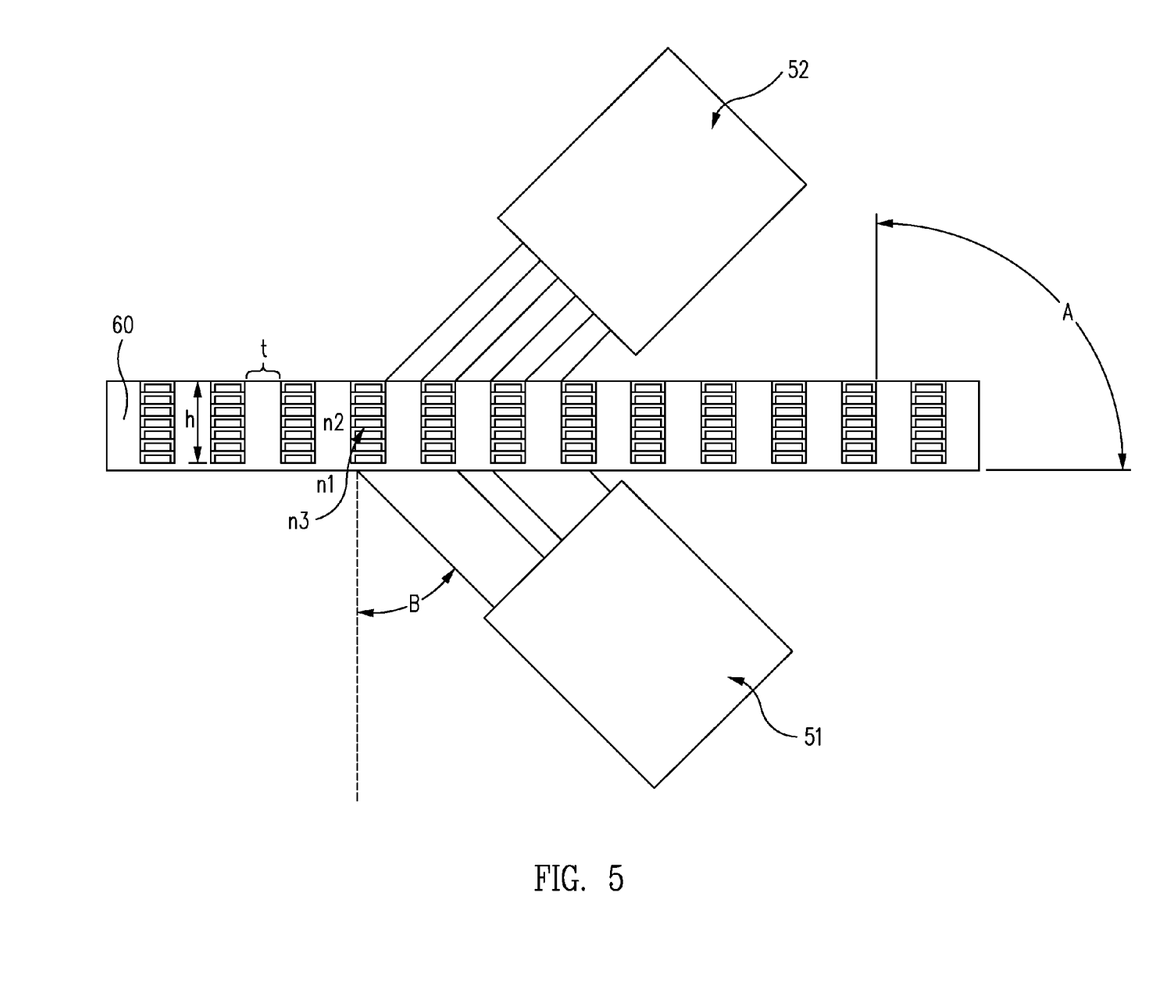
FIG. 5 is a schematic diagram of the illumination, imaging and the measuring and/or sensing system in accordance with the principles of this invention.

FIG. 5 is a schematic representation of the system for measuring and/or sensing binding events between analytes in samples and immobilized ligand arrays in wells as illustrated for example in FIGS. 1-4. Specifically, FIG. 5 shows an illumination subassembly 51 and a measuring and/or sensing subassembly 52 positioned with respect to a multiwell plate in which wells are formed. If the illumination subassembly directs a beam of polarized light at wall 22 in a manner to generate an evanescent field in the plane of the arrays, binding events between analytes in the various samples and the corresponding immobilized ligand arrays are imaged as a pattern of localized changes in the phase of s- and p-polarized reflected light in a manner analogous to that described in U.S. Pat. No. 6,594,011, which has been previously incorporated by reference herein.

It is noted that the illumination subassembly directs a beam of light into the underside of the plate into the material of the plate between wells. In order to achieve total internal reflection (TIR) for imaging the pattern of binding events on the side walls of wells as illustrated in FIG. 5, the indices of refraction of the materials as well as the angle between the transmission surface and the TIR surface is important because TIR cannot occur unless the following equation is satisfied:

$$\sin(A) * \sqrt{n_2^2 - n_1^2 \sin^2(B)} - \cos(A) * n_1 \sin(B) \geq n_3$$

where A is the angle between the transmission surface contacting air and the TIR surface contacting the sample, B is the incidence angle of the light in air, $n_1$ is the index of refraction of air, $n_2$ is the index of refraction of the transparent material of the plate and $n_3$ is the index of refraction of the sample (e.g., water, blood, urine, etc.). This formula simplifies dramatically if the wall of the well is normal to the bottom of the plate since then A=90° and the second term in the above equation vanishes. The resulting equation becomes:

$$\sin(B) \leq \frac{1}{n_1} \times \sqrt{n_2^2 - n_3^2}$$

In one embodiment compatible with current multiwell plate technology, individual wells of the plate are spaced according to Ansi/SBS standards (e.g., 4.5 mm center to center for 384 well plates and 9 mm center to center for 96 well plates). The spacing of the wells is true to standard. However, there is a minimum sidewall thickness in at least one dimension to allow total internal reflection to occur at precisely the critical angle from the side wall in such a way that the entire surface may be illuminated. This minimum thickness, labeled "t" in FIG. 5, depends on the index of refraction of the plate, the index of refraction of the material inside the wells during a measurement, and the depth of the wells. The formula for sidewall thickness in the direction of light propagation is the following:

$$t \geq \frac{h\sqrt{n_2^2 - n_3^2}}{n_3}$$

where t is the sidewall thickness, h is the well depth, $n_2$ is the index of refraction of the plate and $n_3$ is the index of refraction of the (sample) material inside the well during measurement. All variables in the equation are labeled in FIG. 5. For example, for plastic plates having a refractive index of 1.49, a well depth of 10.0 mm, and containing a liquid sample having a refractive index of 1.34, the minimum thickness is about 4.86 mm So for refractive indices of acrylic plates and typical biological fluid samples, the depth of the wells cannot be substantially more than double the sidewall thickness. Additionally, TIR would work for any sample index below 1.34 for the sample material since the same angle would be in the TIR regime.

A 3D stack of arrays may be formed on the faces of a transparent post in a well as disclosed in co-pending U.S. application Ser. No. 11/696,369, filed Apr. 4, 2007 and assigned to the assignee of the present application. The stack of sample chambers may be inserted into the well to surround the post in a manner to position a sample chamber in alignment with an array of the stack of arrays formed on the post.

Parts such as insert 25, shown in FIGS. 2-4, are routinely manufactured by plastic injection molding processes. Some common materials used are polycarbonate, ABS, unfilled nylon 66, polypropylene, polystyrene and polyethylene. The molding accuracy is limited by both standard machining tolerances of 0.001"-0.003" plus an additional tolerance for the molding process based on the resin selected. For example, polycarbonate or ABS adds an additional 0.002" tolerance per inch part dimension. Nylon is 0.003" per inch and polypropylene is an additional 0.005" per inch. For very small parts, less than 0.5 cubic inches, the additional tolerances due to shrinkage and stress are less of an issue. Although walls as thin as 0.004" can be made with injection molding, they require very high pressures and typically, the minimum wall thickness is closer to 0.03". DIN 16901 standards provide specific general tolerances and dimensions for general-purposes injection molding, technical injection-molding and high-precision injection-molding. Sharp edges should also be avoided since the recommended minimum radius is one-fourth of the minimum wall thickness.

Figure 6A:
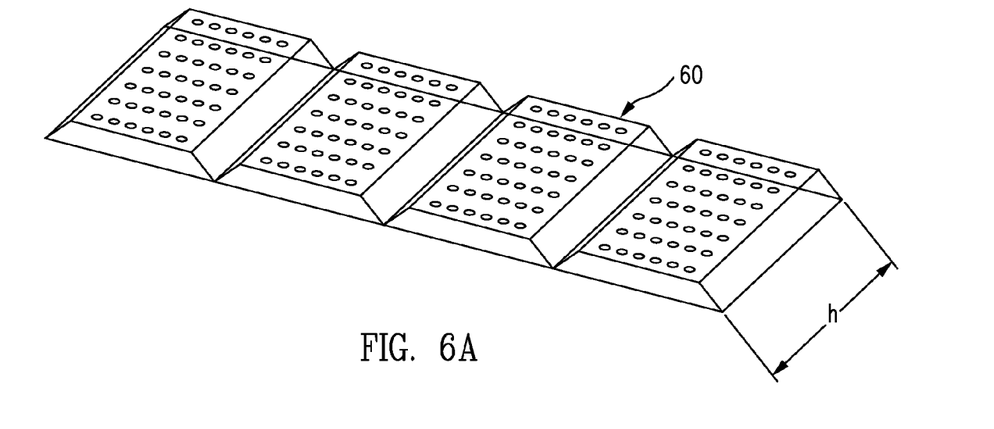
FIGS. 6A-6C illustrate an arrangement for forming patterns of immobilized ligand arrays within the wells.
Figure 6B:
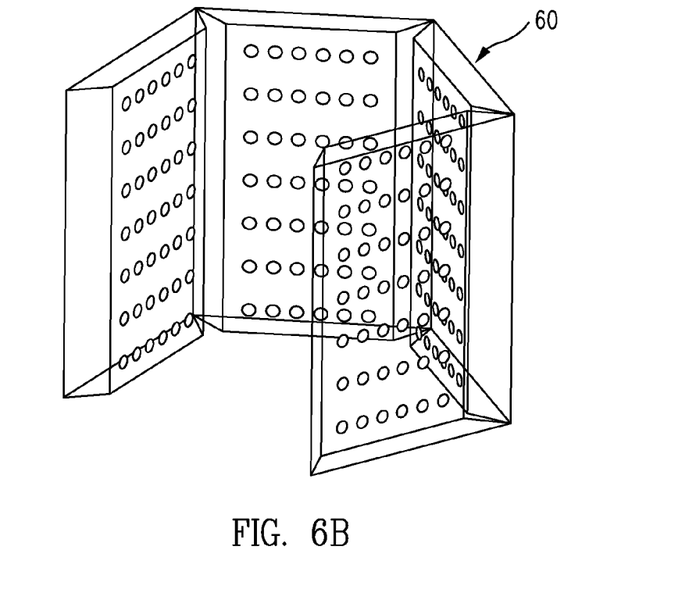
Figure 6C:
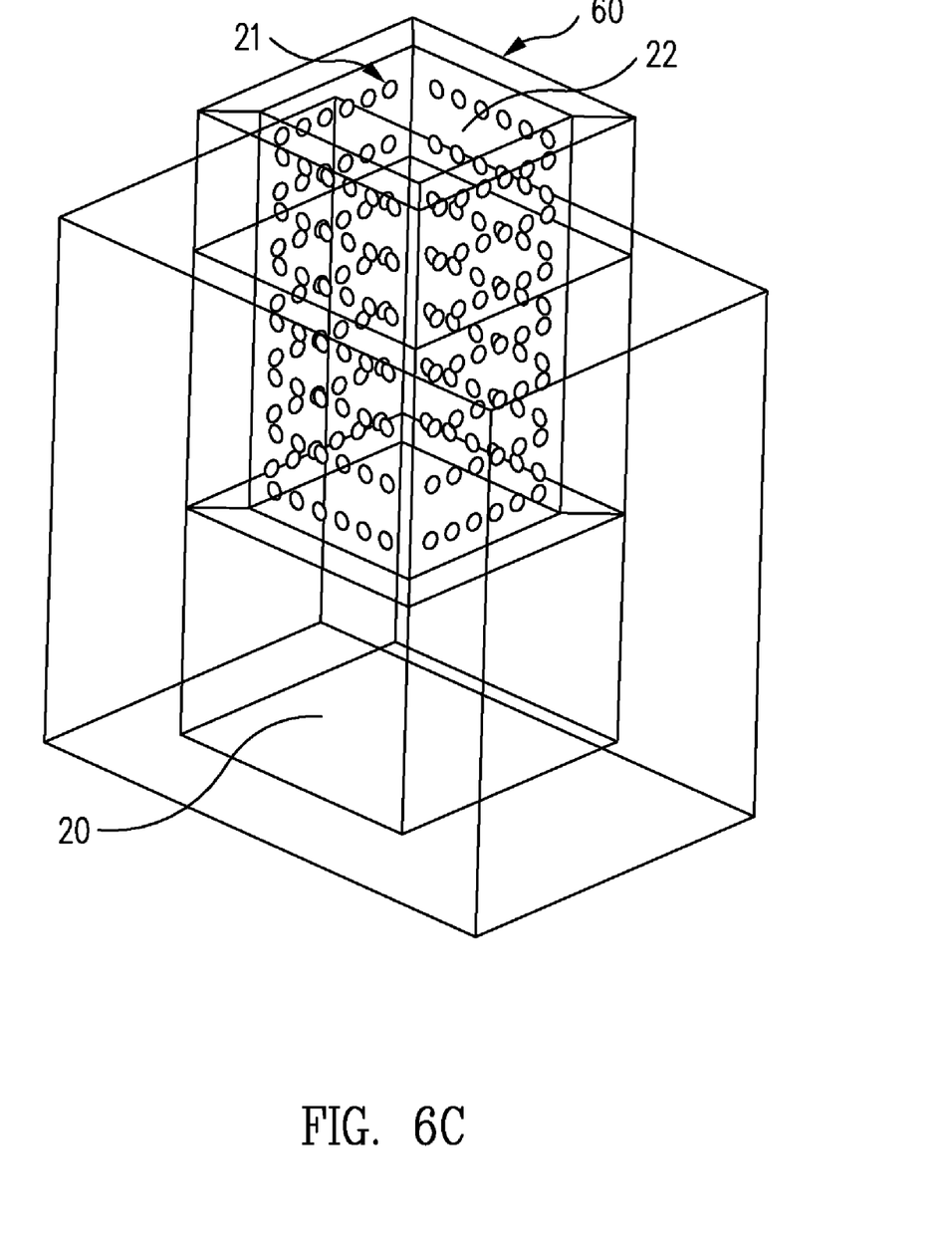

The arrays may be immobilized illustratively on the planar surfaces of a flexible substrate 60 as illustrated in FIGS. 6A-6C. In this arrangement, spots are printed on a "liner" substrate comprised of, for example, a flat piece of glass or plastic, and folded to provide the spots within a well. The liner substrate is then attached to a larger plate in such a way that the polarization of the light source does not change significantly when passing through the mated interface. The substrate width, labeled h in FIG. 6A, is equal to the well depth and is closed into a square tube geometry (FIG. 6C) for insertion as a liner into a well of a plate. A single array may be applied to each wall of the tube or to a selected wall of the tube. Multiple arrays may be applied directly to each or all walls of a well or selected wells or walls. It is intended that all variations are within the scope of the present invention and that they be encompassed by the language of the claims. It is to be understood that the liner and the well into which a liner is inserted need not have a square geometry. The geometry may (for example) be rectangular, hexagonal, octagonal, etc. as discussed in the definitions. The well need only have a single planar side wall and the liner insert, with arrays immobilized, need only match the well geometry. Moreover, a liner may be positioned around a sample stack insert prior to placement into a well.

It is to be understood also that polarized light need not be used herein. It is intended that any measuring and/or sensing technique using an illumination source in a manner to achieve total internal reflection and an evanescent field in the plane of an array or arrays of ligands on a planar side wall of a well be encompassed by the following claims.

The foregoing description of exemplary and preferred embodiments is presented for purposes of illustration and disclosure in accordance with the requirements of the law. It is not intended to be exhaustive or to limit the invention to the precise form(s) described, but only to enable others skilled in the art to understand how the invention may be suited for a particular use or implementation. The possibility of modifications and variations will be apparent to practitioners skilled in the art. This disclosure has been made with respect to the current state of the art, but also contemplates advancements and that adaptations in the future may take into consideration those advancements, namely in accordance with the then current state of the art. It is intended that the scope of the invention be defined by the claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component or step is explicitly recited in the claims.

What is claimed is:

1. A plate of transparent material, the plate comprising:
a well having at least one upstanding wall, said wall having a strata of ligand arrays formed thereon, wherein each array of said strata of ligand arrays is formed in a spaced apart position along an upstanding axis of said wall; and
a side portion defining said wall, said side portion being of a geometry to permit a beam of light to be directed into said wall in a manner to achieve total internal reflection at said wall and generate an evanescent field at said wall.

2. The plate as in claim 1, wherein each array of said strata of arrays is formed in a spaced apart position along the vertical axis of said wall.

3. The plate as in claim 1, further comprising a stack of chambers, each of said chambers being of a geometry to insert into said well, each of said chambers occupying a position in said well corresponding to one of said arrays.

4. The plate as in claim 3, wherein each chamber includes an aperture for introducing a sample in a manner to expose each sample to an associated one of said arrays.

5. The plate as in claim 3, wherein said stack of chambers is formed in a single structure.

6. The plate as in claim 3, wherein said stack of chambers includes a plurality of individual cells.

7. The plate as in claim 3, wherein each of said chambers has at least one open side wall in a position and is of a geometry to match an associated one of said arrays.

8. The plate as in claim 1, further comprising a plurality of wells, each of said wells having a side wall having immobilized thereon a stratum of arrays of ligands stacked along the vertical axis of the side wall.

9. The plate as in claim 8, wherein each of said wells includes a transparent liner and said liner forms said side wall.

10. The plate as in claim 8, wherein each of said plurality of wells has a plurality of side walls each having immobilized thereon a stratum of arrays of ligands stacked along the vertical axis of the side wall.

11. The plate as in claim 1, further comprising a plurality of wells, at least one of the wells having at least a first planar side wall, said first planar side wall having immobilized thereon a strata of ligand arrays stacked along the vertical axis of the well, said well including a plurality of membranes, said membranes being positioned in a stack with the membranes being spaced apart such that adjacent ones of said membranes form a chamber therebetween positioned to correspond to one of said immobilized arrays.

12. A plate of transparent material, the plate comprising:
a well having at least one wall, said wall having a strata of ligand arrays formed thereon;
a side portion defining said wall, said side portion being of a geometry to permit a beam of light to be directed into said wall in a manner to achieve total internal reflection at said wall and generate an evanescent field at said wall; and
a stack of chambers, each of said chambers being of a geometry to insert into said well, and each of said chambers occupying a position in said well corresponding to one of said arrays.

13. The plate as in claim 12, wherein each chamber includes an aperture for introducing a sample in a manner to expose each sample to an associated one of said arrays.

14. The plate as in claim 12, wherein said stack of chambers is formed in a single structure.

15. The plate as in claim 12, wherein said stack of chambers includes a plurality of individual cells.

16. The plate as in claim 12, wherein each of said chambers has at least one open side wall in a position and is of a geometry to match an associated one of said arrays.

17. The plate as in claim 12, wherein said well includes a transparent liner and said liner forms said side wall.

18. The plate as in claim 12, further comprising a plurality of wells, each of said wells having a side wall having immobilized thereon a stratum of arrays of ligands stacked along the vertical axis of the side wall.

19. A plate for imaging, the plate comprising:
a well having at least one wall, said wall having a strata of ligand arrays formed thereon and having a geometry to permit a beam of light to be directed into it in a manner to achieve total internal reflection at said wall and generate an evanescent field at said wall; and an insert including a stack of chambers, each chamber having at least one open sidewall aligned with one of the ligand arrays.

20. A system for imaging, comprising:

a plate including a well having at least one wall, said wall having a strata of ligand arrays formed thereon; and an insert including a stack of chambers, each of the chambers having at least one open side wall aligned with one of the ligand arrays;

a light source that provides a beam of light into the wall in a manner to achieve total internal reflection at said wall and generate an evanescent field at said wall; and an imaging apparatus that images light reflected from the wall.

* * * * *